United States Patent [19]

Williams et al.

[11] Patent Number: 5,632,972
[45] Date of Patent: *May 27, 1997

[54] METHOD FOR TREATING GINGIVAL AND PERIODONTAL TISSUES

[75] Inventors: David R. Williams, Monroe; Christine W. Ryles, Milford; Stephen R. Barrow, Trumbull, all of Conn.

[73] Assignee: Chesebrough-Pond's USA Co., Division of Conopco, Inc., Greenwich, Conn.

[ * ] Notice: The term of this patent shall not extend beyond the expiration date of Pat. No. 5,616,313.

[21] Appl. No.: 269,429

[22] Filed: Jun. 30, 1994

[51] Int. Cl.⁶ ............................ A61K 7/16; A61K 7/18; A61K 7/20; A61K 33/40
[52] U.S. Cl. .................. 424/49; 424/52; 424/53; 424/613; 424/614; 424/615; 424/616; 424/641; 424/642; 424/643; 424/717
[58] Field of Search .......................... 424/49–58

[56] References Cited

U.S. PATENT DOCUMENTS

| | | |
|---|---|---|
| 3,888,976 | 6/1975 | Mlkvy et al. ............ 424/44 |
| 3,935,305 | 1/1976 | Delaney et al. . |
| 3,937,803 | 2/1976 | Delaney et al. . |
| 3,937,804 | 2/1976 | Delaney et al. . |
| 3,943,240 | 3/1976 | Delaney et al. . |
| 4,022,880 | 5/1977 | Vinson et al. . |
| 4,100,269 | 7/1978 | Pader . |
| 4,160,022 | 7/1979 | Delaney et al. . |
| 4,160,821 | 7/1979 | Sipos ........................ 424/49 |
| 4,226,851 | 10/1980 | Sompayrac . |
| 4,229,430 | 10/1980 | Fahim et al. ............... 424/49 |
| 4,477,438 | 10/1984 | Willcockson et al. . |
| 4,487,757 | 12/1984 | Kiozpeoplou . |
| 4,528,180 | 7/1985 | Schaeffer . |
| 4,537,765 | 8/1985 | Gaffar et al. . |
| 4,547,362 | 10/1985 | Winston et al. . |
| 4,557,935 | 12/1985 | af Ekenstam et al. . |
| 4,575,457 | 3/1986 | Mazarin . |
| 4,623,536 | 11/1986 | Winston et al. . |
| 4,647,452 | 3/1987 | Ritchey et al. . |
| 4,687,663 | 8/1987 | Schaffer . |
| 4,788,052 | 11/1988 | Ng et al. . |
| 4,837,008 | 6/1989 | Rudy et al. . |
| 4,839,156 | 6/1989 | Ng et al. . |
| 4,839,157 | 6/1989 | Mei-King Ng et al. . |
| 4,849,213 | 7/1989 | Schaeffer . |
| 4,937,066 | 6/1990 | Vlock . |
| 4,943,429 | 7/1990 | Winston et al. . |
| 5,015,466 | 5/1991 | Parran, Jr. et al. . |
| 5,015,467 | 5/1991 | Smitherman . |
| 5,037,633 | 8/1991 | Ziemkiewicz et al. . |
| 5,037,634 | 8/1991 | Williams et al. . |
| 5,059,417 | 10/1991 | Williams et al. . |
| 5,085,853 | 2/1992 | Williams et al. ............. 424/53 |
| 5,094,845 | 3/1992 | Vlock . |
| 5,104,644 | 4/1992 | Douglas . |
| 5,165,914 | 11/1992 | Vlock . |
| 5,186,926 | 2/1993 | Williams et al. ............. 424/53 |
| 5,217,710 | 6/1993 | Williams et al. ............. 424/52 |
| 5,252,312 | 10/1993 | Gentile et al. .............. 424/44 |
| 5,300,305 | 4/1994 | Stapler et al. ............. 424/490 |
| 5,302,373 | 4/1994 | Giacin et al. .............. 424/49 |
| 5,372,802 | 12/1994 | Barrows et al. ............ 424/52 |
| 5,372,803 | 12/1994 | Williams et al. ............ 424/53 |
| 5,392,947 | 2/1995 | Gentile ..................... 220/665 |

*Primary Examiner*—Shep K. Rose
*Attorney, Agent, or Firm*—Milton L. Honig

[57] ABSTRACT

A method for minimizing damage to gingival and periodontal tissue is provided through steps that include delivering a first composition containing a zinc salt to a receptacle, delivering a second composition containing a bicarbonate salt to the same receptacle, and transferring within five minutes of delivery to the receptacle the combination into the mouth onto the gingival and periodontal tissues. Where the compositions are semi-solid such as in a toothpaste and/or gel, the receptacle is ordinarily a toothbrush. Liquid compositions such as mouthrinses may employ an expectorant cup as a receptacle.

7 Claims, No Drawings

METHOD FOR TREATING GINGIVAL AND PERIODONTAL TISSUES

BACKGROUND OF THE INVENTION

1. Field of the Invention

The invention concerns a method for treating gingival and periodontal tissues.

2. The Related Art

The importance of maintaining proper gingival and periodontal health has been well established. The factors normally evaluated in determining the health of a patient's periodontium are the following:

(1) gingival tone, texture and consistency;

(2) gingival attachment as measured in the sulcus (6 reference points about each tooth) with a calibrated periodontal probe;

(3) gingival enlargement;

(4) gingival bleeding when provoked by instrumentation (amount and length of time of bleeding);

(5) the presence of chronic destructive periodontal disease which, if advanced, will threaten loss of dentition, i.e. severe bone loss, tooth mobility, deep pocket formation, bleeding, etc.;

(6) the presence of pain or discomfort to the patent.

Treatment of the foregoing may comprise regular and periodic massaging of the gingivae, tooth brushing and rinsing of the mouth on a regular basis, deep scaling and curettage procedures performed by dentists, bacterial control and in extreme cases, surgical procedures may become necessary.

Oral compositions containing both a peroxide and sodium bicarbonate have been reported as excellent curative and preventative systems against gum disease. Dr. Paul H. Keyes has long advocated use of such systems to the dental profession and to the public at large. For instance, see Keyes et al. "Periodontics and Oral Hygiene", January 1978, pages 51–56. Formulations based on the Keyes technology, especially the peroxide component, are particularly prone to decomposition. A quite successful approach to the decomposition problem has involved physical separation of the peroxide into a compartment separate from co-reactive ingredients. U.S. Pat. Nos. 4,849,213, 4,687,663 and 4,528,180, all to Schaeffer, disclose packages with a dual compartment respectively storing a peroxide and a bicarbonate composition. Improvements in this technology have been reported in U.S. Pat. Nos. 5,037,633, 5,037,634, 5,059,417, 5,085,853 and 5,217,710 all having inventorship by Williams and coworkers.

In U.S. Pat. Nos. 4,788,052, 4,839,156 and 4,839,157 (all to Ng et al) are described aqueous hydrogen peroxide gel dentifrices that can be stabilized by use of a combination of hydrophilic and hydrophobic fumed silica.

Aqueous mouthrinses have been described in U.S. Pat. No. 5,104,644 (Douglas) that contain hydrogen peroxide. Present at relatively low concentrations are also such additives as zinc chloride, surfactant, sodium citrate and citric acid. Hydrogen peroxide is stated to function as the principal active ingredient against anaerobic organisms and to assist removing microbiota through the mechanical actions of bubbling and foaming. Zinc chloride is incorporated for the stated purpose of astringency in combination with the peroxide to help edematous gingiva return to a more normal state. Sodium citrate is present for the stated purpose of being an anticoagulant for healing hemorrhagic tissue. Levels of zinc chloride in these compositions range from 0.02% to 0.8% by weight.

Control of gingivitis has also been reported in U.S. Pat. No. 4,575,457 (Mazarin) through use of a composition containing a skin respiratory factor (SRF) along with sodium chloride, bicarbonate, fluoride and zinc chloride.

Germicidal effects of hydrogen peroxide in combination with zinc salts have been reported in U.S. Pat. No. 4,557,935 (Af Ekenstam et al.). Combinations of zinc and peroxide have also been reported in U.S. Pat. No. 4,477,438 (Wilcoxon et al.) and in a series of patents to Vlock, namely U.S. Pat. Nos. 4,937,066, 5,094,845 and 4,165,914.

As seen from the aforementioned list of references, there has been considerable progress in the art. However, none of these described systems have been fully effective against gingival and periodontal problems while being both safe and aesthetically consumer acceptable.

Accordingly, it is an object of the present invention to provide a method for the treatment of gingival and periodontal disease.

It is another object of the present invention to provide a method for preventing gingival bleeding, gum recession and loss of gingival tone, texture or consistency.

It is still another object of the present invention to provide a method for the treatment and prevention of gum disease that does not stain teeth, contains no chlorinated actives and in all ways is safe and effective.

It is a still further object of the present invention to provide a method for the treatment and prevention of gum disease through use of a composition that not only is effective but also minimizes taste problems often associated with astringent materials.

These and other objects of the present invention will become more readily apparent upon consideration of the more detailed description and Examples which follow.

SUMMARY OF THE INVENTION

A method is reported for inhibiting gingival bleeding and improving texture and consistency of gingival and periodontal tissues in a procedure which includes:

(i) delivering a first composition to a receptacle such as an expectorant cup or toothbrush, the first composition comprising from about 0.1 to about 10% by weight of zinc salt in a pharmaceutically acceptable carrier;

(ii) delivering a second composition to the receptacle, the second composition comprising from about 1 to about 80% by weight of a bicarbonate salt in a pharmaceutically acceptable carrier;

(iii) transferring from the receptacle into the mouth a combination of the first and second compositions within five minutes of their delivery to the receptacle; and (iv) agitating the combination of first and second compositions within the mouth against the gingival and periodontal tissues.

Also reported is a method for inhibiting gingival bleeding and improving the texture and consistency of gingival and periodontal tissues in a procedure which includes:

(i) extruding a first composition onto a toothbrush, the first composition comprising from about 0.1 to about 10% by weight of zinc salt in a pharmaceutically acceptable carrier;

(ii) extruding a second composition onto the toothbrush comprising from about 1 to about 80% by weight of a bicarbonate salt in a pharmaceutically acceptable carrier; and (iii) brushing gingival and periodontal surfaces surrounding the teeth simultaneously with a combination of the first and second compositions.

In a preferred embodiment, the first composition can also include a peroxygen compound. Another embodiment utilizes ascorbic or citric acids in place of the peroxygen compound.

DETAILED DESCRIPTION

Now it has been discovered that a combination of zinc and bicarbonate salts deliver a very potent inhibitory effect against gingival and periodontal tissue damage. It has been further established that such effect requires the zinc and bicarbonate salts to be separately packaged prior to their introduction into the oral cavity. A dual compartment dispenser into which the respective actives are placed provides a suitable vehicle for delivery of the combined zinc and bicarbonate compositions.

Thus, as a first essential component there is required a salt delivering zinc ions. By the term "zinc ion" is meant that the zinc-atom portion of a molecule of the zinc compound in the solid or undissociated state, is capable of being dissociated into simple or complex zinc ions, especially when dispersed in an aqueous medium. Examples of the compounds that may be employed are zinc salts of the following inorganic ions: borate, bromide, carbonate, hexofluorosilicate, pyrophosphate, silicate, sulphate and titanate. Organic anions are those having from 2 to 22 carbon atoms with a charged group selected from carboxylate, sulphonate, sulphate and phosphate. Specific examples include, but are not limited to, acetate, benzoate, citrate, glycinate, lactate, phenolsulphonate, salicylate, tartrate, acetylacetonate, maleate, succinate, ascorbate, and gluconate. Most preferred is zinc citrate, which may be in hydrated form.

The zinc salts will generally be present in the dental compositions of the present invention in an amount from about 0.05 to about 10%, preferably between about 0.2 and 5%, optimally between about 0.8 and 3% by weight.

Oral compositions of the present invention may be in the form of either a toothpaste, gel or mouthwash.

The term "pharmaceutically acceptable carrier" will include such functional ingredients as water, humectants, abrasives, thickeners and surfactants. Total levels of these material may range anywhere from about 20 to about 99% by weight.

The first composition, i.e. the composition with zinc salt, preferably is a gel. Advantageously, the gel will include a peroxygen compound such as hydrogen peroxide, urea peroxide, calcium peroxide and the salts of perborate, persilicate, perphosphate and percarbonate. The most suitable for this invention is hydrogen peroxide. The amount of the peroxygen compound may range from about 0.1 to about 10% by weight. In terms of active weight hydrogen peroxide, the amount will range from about 0.5 to about 5%, preferably from about 0.8 to about 4%, optimally between about 1 and 3% by weight.

Instead of a peroxygen compound, the first composition may contain a $C_2$–$C_{20}$ carboxylic acid. Illustrative acids include citric, malic, lactic and ascorbic acids. Levels of the acids may range in amounts similar to that of the peroxygen compound, i.e. from about 0.1 to about 10% by weight. Citric acid is most preferred. When present, these acids will either be in liquid, gel or paste type compositions.

Advantageously, the pH of the first composition will be held between about 3.2 and 5.0, preferably from 4.0 to 4.5.

Another component of the first composition may be a fluoride anticaries compound. Illustrative of fluoride compounds are sodium fluoride, potassium fluoride, calcium fluoride, magnesium fluoride, stannous fluoride, stannous monofluorophosphate, sodium monofluorophosphate and copper fluoride. These sources should release anywhere from about 25 to 3500 ppm of fluoride ion. The anticaries agent will be present in an amount from about 0.01 to about 5%, preferably from about 0.1 to about 2.5%, optimally between about 0.2 and about 1.5% by weight of the first composition.

Water may be present in the compositions in amounts ranging from about 20 to about 95% by weight. When the peroxide composition is a gel, the amount of water may range from about 30 to about 55%, optimally between about 35 and 45% by weight. Anhydrous first and second compositions may also be suitable.

Structurants are necessary where the first composition is in the form of a gel. Most suitable as the structurant are the polyoxyethylene-polyoxypropylene copolymers where the hydrophobic portion, represented by $(C_3H_6O)$, has a molecular weight ranging from about 2,750 to 4,000 and the hydrophilic portion, represented by $(C_2H_4O)$, constitutes about 70 to 80% of the weight of the copolymer. Commercially the copolymers are available from the BASF Corporation under the trademark, Pluronic® F88, F99, F108 and F127. Most preferred is Pluronic® F127 (hereinafter referred to by its CTFA name, Poloxamer 407®) which has a molecular weight ranging from about 10,000 to 15,000, and containing about 70% of the hydrophilic polyoxyethylene moiety. Amounts of the copolymer can range anywhere from 18 to 25% by weight, preferably between 19 and 24%. Poloxamers are particularly suitable for this invention because of their wide pH tolerance, good compatibility with hydrogen peroxide and unique gel properties.

Glycerol is another preferred ingredient of the first composition when in gel or liquid rinse form. Amounts of glycerol may range from about 5 to about 50%, preferably between about 5 to about 20% by weight for the rinse but preferably between about 35 and 45% by weight for the gel.

Adjunct minor ingredients may also be present in the first composition of this invention. Included may be small amounts of colorant, flavor and antioxidant.

Oral compositions of the present invention will include, besides a first composition, an additional separate bicarbonate-containing second composition, each held within a separate compartment or each segregated within a single compartment (e.g. peroxide encapsulated) available for simultaneous delivery in substantially equal volumes for use in the mouth.

The bicarbonate second composition may also contain a fluoride anticaries compound selected from the same fluoride compounds in essentially identical amounts to those described hereinabove with respect to the first composition. Especially preferred is sodium fluoride. Bicarbonate salts will be present in alkali metal form, examples of which are sodium and potassium. Typically, the concentration of bicarbonate salt will range from about 0.5 to about 80%, preferably from about 5 to about 50%, optimally between about 8 and about 20% by weight. The pH of the bicarbonate composition may range from about 7.0 to about 9.5, most preferably about 8.0 to 9.0. When the bicarbonate composition is in toothpaste or gel form, there will typically be included a natural or synthetic thickening agent in an amount from about 0.1 to 10%, preferably about 0.5 to 5% by weight. Thickeners may include hydroxypropyl methyl cellulose, hydroxyethyl cellulose, sodium carboxymethyl cellulose, xanthan gum, tragacanth gum, karaya gum, arabic gum, Irish moss, starch, alginates and carrageenans.

Surfactants are normally also included in the bicarbonate compositions. These surfactants may be of the anionic, nonionic, cationic or amphoteric type. Most preferred are sodium lauryl sulfate, sodium dodecylbenzene sulfonate and sodium lauryl sarcosinate. Surfactants are usually present in an amount from about 0.5 to about 5% by weight.

When in the form of a toothpaste or gel, the bicarbonate compositions will normally include an abrasive in addition to the bicarbonate. Abrasives may be selected from water-insoluble alkali or alkaline earth metal salts of metaphosphate (IMP), calcium carbonate, aluminate and silicate. Especially preferred are silica, dicalcium phosphate and calcium carbonate. Amounts of the abrasive will range from about 5 to about 80% by weight.

Flavors are usually present in both the first and, when suitable, second compositions. These flavors may be based on oils of spearmint and peppermint. Examples of other flavoring materials include menthol, clove, wintergreen, eucalyptus and aniseed. Flavors may range in concentration from about 0.1 to about 5% by weight of the total composition.

Sweetening agents such as saccharin, sodium cyclamate, aspartame, sucrose and the like may be included at levels from about 0.1 to about 5% by weight of the total composition.

Other additives may also be incorporated into the oral compositions including preservatives, silicones, other synthetic or natural polymers such as Gantrez S-97®, and antitartar actives such as tetrapotassium or tetrasodium pyrophosphates.

Relative weight amounts of the first composition to that of the second composition will range from about 1:2 to 2:1, preferably about 1:1. Each component may be kept isolated in a separate compartment of a dispenser. Advantageously, the dispenser will simultaneously deliver approximately equal amounts of each composition through an orifice at whose end the separate compositions may intermingle. Suitable for this purpose are dual-compartment packages such as described in the Schaeffer patents, U.S. Pat. No. 4,528,180 and U.S. Pat. No. 4,849,213. Most preferred is where the first composition is in the form of a gel and the second composition is in the form of an opaque paste.

The following examples will more fully illustrate the embodiments of this invention. All parts, percentages and proportions referred to herein and in the appended claims are by weight of the total composition unless otherwise stated.

EXAMPLE 1

The method of the present invention can typically be practiced through use of a zinc salt composition whose formulation is detailed under Table I. The formulation of Table I may be utilized in combination with a bicarbonate composition detailed under Table II, each of the compositions being held in a separate compartment of a dual-compartment dispenser.

TABLE I

Zinc Salt Composition

| Ingredient | Wt. % |
|---|---|
| Pluronic F127 | 20.000 |
| Glycerin | 40.000 |
| Hydrogen Peroxide (35% food grade) | 4.285 |
| Zinc Citrate | 4.000 |
| Methyl Salicylate | 0.500 |
| Sodium Fluoride | 0.240 |
| Phosphoric Acid (85% w/w) | 0.150 |
| FD&C Blue 1 | 0.005 |
| Deionized water | Balance |

TABLE II

Bicarbonate Paste Composition

| Ingredient | Wt. % |
|---|---|
| Polyol II (sorbitol and other sugars) | 48.710 |
| Syloid 63XX (abrasive silica) | 15.000 |
| Sodium Bicarbonate | 10.000 |
| PEG 32 (polyethylene glycol) | 5.000 |
| Sylox 15x (thickening silica) | 4.600 |
| Sodium Lauryl Sulfate | 2.980 |
| SD Alcohol 38B | 2.850 |
| Cellulose Gum | 0.800 |
| Menthol | 0.500 |
| Sodium Saccharin | 0.500 |
| Titanium Dioxide | 0.300 |
| Sodium Fluoride | 0.230 |
| Deionized water | Balance |

EXAMPLE 2

This example illustrates a liquid mouthwash suitable for practicing the method of the present invention. A zinc salt containing first liquid and a sodium bicarbonate containing second liquid are prepared with the following compounds:

| Components | First Liquid | Second Liquid |
|---|---|---|
| Ethanol | — | 24.0 |
| Humectant (Polyol 2) | — | 7.0 |
| Sodium bicarbonate | — | 2.0 |
| Solubilizer (Polysorbate) | — | 0.4 |
| Flavor | — | 0.4 |
| Hydrogen peroxide (35% sol.) | 4.3 | — |
| Zinc Citrate | 4.0 | — |
| Dye | 0.003 | — |
| Saccharin | — | 0.07 |
| Sodium lauryl sulphate | — | 0.6 |
| Phosphoric acid | 0.04 | — |
| Deionized water | balance | balance |

Equal amounts of the liquids are added to a dual compartment rinse dispenser such as shown in FIGS. 1 to 3 of U.S. Pat. No. 5,252,312 (Gentile et al.) or U.S. Pat. No. 5,289,950 (Gentile et al.). The liquids after being dispensed from the package combine to form an effervescent mouthwash.

EXAMPLE 3

This Example illustrates a dual-paste dentifrice suitable for practicing the method of the present invention. A zinc lactate containing first paste and a sodium bicarbonate containing second paste were prepared with the following components:

TABLE I

| COMPONENTS | FIRST PASTE | SECOND PASTE |
| --- | --- | --- |
| Glycerol | 26.0 | 33.0 |
| Sorbitol (70% Aqueous) | 27.9 | — |
| Sodium Carboxymethyl Cellulose | — | 0.8 |
| Xanthan Gum | 0.5 | — |
| Silica Thickener | 3.0 | 0.5 |
| Sodium Benzoate | 0.1 | 0.5 |
| Sodium Saccharin | — | 0.2 |
| Zinc Lactate | 2.0 | — |
| Calcium Metaphosphate | 30.0 | 17.5 |
| Calcium Carbonate | — | 2.5 |
| Sodium Bicarbonate | — | 20.0 |
| Citric Acid | 4.5 | — |
| Flavor | — | 1.0 |
| Sodium Fluoride | 0.24 | 0.24 |
| Water | balance | balance |

Equal amounts of the first and second pastes are added to respective chambers of a dual compartment dispenser such as shown in U.S. Pat. No. 5,038,963 (Pettingill et al.) and U.S. Pat. No. 5,020,694 (Pettingill). When a consumer is ready for use of this product, the consumer applies pressure to the dispenser thereby causing extrusion of strands of the first and second pastes which are deposited onto a toothbrush. Within one or two minutes, the consumer will apply the toothbrush with the combined first and second components to the teeth and gums brushing same.

EXAMPLE 4

A clinical trial was conducted to compare the dental product of Example 1 with an identical product that did not include bicarbonate/zinc citrate combination.

Methodology

Subject Selection Criteria

Forty panelists, both female and male, between the ages of 18 and 65 were recruited to participate in this study. Panelists were chosen on the basis of having present the Mandibular four incisors and two cuspid teeth. Excluded from participation was anyone with a history of serious disease or persons who exhibited gross neglect of oral hygiene, rampant caries, advanced periodontitis or those in need of professional dental attention. Subjects who did not brush their teeth at least two times per day were also excluded.

Study Examinations
Phase One:

Full mouth gingival assessments were evaluated according to Lobene's Modified Gingival Index. Following assessment, each panelist received a thorough dental cleaning by a registered dental hygienist. Panelists were then given a regular toothpaste to use for the following three weeks thereby allowing each panelist to build gingival problems. After three weeks of regular toothpaste use, gingival evaluations were conducted to obtain a baseline for panelists' normal gingival condition.

Another dental prophylaxis was performed rendering the panelists ready to receive the first test product. The product of Example 1 was then used by panelists for the next three weeks. Gingival evaluations were conducted after the two and three week period of product usage.

Phase Two:

Panelists were directed to use regular toothpaste for a four week washout period.

Phase Three:

The teeth were then treated to another prophylaxis. Panelists were then assigned to use Crest® (control sample) for the next three weeks. Gingival evaluations were conducted after two and three week product usage.

Study Procedures:

The study was conducted in a single blind manner with panelists having no knowledge of the identity of the test dentifrices. All data compiled during the course of the study was subjected to appropriate statistical analysis.

Results of the clinical evaluation are outlined in the Table below.

TABLE II

| | Modified Gingival Index (MGI) | | | | |
| --- | --- | --- | --- | --- | --- |
| Shield Teeth | BASELINE | FINAL | Ramfjord Teeth | BASELINE | FINAL |
| Crest® Reg. | .686 | 1.733 | Crest® Reg. | .727 | 1.225 |
| Example 1 | .718 | 1.482 | Example 1 | .687 | 1.090 |
| | 14.5% | | | 11% | |
| | | BLEEDING | | | |
| Crest® Reg. | .177 | .949 | Crest® Reg. | .129 | .304 |
| Example 1 | .193 | .655 | Example 1 | .141 | .222 |
| | 31% | | | 27% | |
| | | PLAQUE | | | |
| Crest® Reg. | | 14.11 | Crest® Reg. | | 8.59 |
| Example 1 | | 12.52 | Example 1 | | 7.94 |
| | 11% | | | 7.5% | |

Based on the results recorded in Table II, it is evident that the dental composition of Example 1 containing bicarbonate/zinc citrate combination significantly reduced bleeding, exhibited a significant improvement in the Modified Gingival Index and had some effect in reducing plaque.

The foregoing description and Examples illustrate selected embodiments of the present invention. In light thereof, various modifications will be suggested to one skilled in the art, all of which are within the spirit and purview of this invention.

What is claimed is:

1. A method for inhibiting gingival bleeding and improving texture and consistency of gingival and periodontal tissues which comprises:

(i) delivering a first liquid composition to a receptacle, the first liquid composition comprising from about 0.1 to about 10% by weight of zinc salt and from about 0.1% to about 10% by weight of peroxygen compound in a pharmaceutically acceptable carrier;

(ii) delivering a second liquid composition to the receptacle, the second liquid composition comprising from about 1 to about 80% by weight of a bicarbonate salt in a pharmaceutically acceptable carrier;

(iii) transferring from the receptacle into the mouth a combination of the first and second liquid compositions within five minutes of their delivery to the receptacle; and (iv) agitating the combination of first and second liquid compositions within the mouth against the gingival and periodontal tissues.

2. A method according to claim 1 wherein the receptacle is selected from the group consisting of a cup and a toothbrush.

3. A method according to claim 1 wherein the peroxygen compound is selected from the group consisting of hydrogen peroxide, urea peroxide, calcium peroxide and the salts of perborate, persilicate, perphosphate and percarbonate.

4. A method according to claim 1 wherein the second composition further comprises a fluoride source present in an effective amount to inhibit formation of caries on teeth.

5. A method according to claim 1 wherein the zinc salt is zinc citrate.

6. A method according to claim 1 wherein the first liquid composition has a pH ranging from 3.2 to 5.0.

7. A method according to claim 1 wherein the relative weight ratio of the first liquid composition to the second liquid composition ranges from about 1:2 to 2:1.

* * * * *